United States Patent [19]
Newkirk et al.

[11] Patent Number: 5,971,913
[45] Date of Patent: Oct. 26, 1999

[54] NOISE AND LIGHT MONITOR APPARATUS

[75] Inventors: David C. Newkirk, Harrison, Ohio; John J. Kody, New Palestine, Ind.; Michael M. Donnelly; D. Scott Prows, both of Cincinnati, Ohio

[73] Assignee: Hill-Rom, Inc., Batesville, Ind.

[21] Appl. No.: 08/926,381

[22] Filed: Sep. 9, 1997

Related U.S. Application Data

[63] Continuation-in-part of application No. 08/533,371, Sep. 25, 1995, Pat. No. 5,817,003.
[51] Int. Cl.$^6$ ..................................................... A61G 11/00
[52] U.S. Cl. .................................................................. 600/22
[58] Field of Search ........................................... 600/21–22

[56] References Cited

U.S. PATENT DOCUMENTS

| | | |
|---|---|---|
| D. 375,792 | 11/1996 | Hillman et al. . |
| 3,187,744 | 6/1965 | Dorsak et al. . |
| 4,161,172 | 7/1979 | Pickering . |
| 4,750,474 | 6/1988 | Dukhan et al. . |
| 5,081,722 | 1/1992 | Yu . |
| 5,162,038 | 11/1992 | Wilker . |
| 5,339,223 | 8/1994 | Kremenchugsky et al. . |
| 5,400,425 | 3/1995 | Nicholas et al. . |
| 5,446,934 | 9/1995 | Frazier . |
| 5,453,077 | 9/1995 | Donnelly et al. . |

FOREIGN PATENT DOCUMENTS

| | | |
|---|---|---|
| 49-122184 | of 1974 | Japan . |
| WO 83/01189 | 4/1983 | WIPO . |
| WO 90/09771 | 9/1990 | WIPO . |

OTHER PUBLICATIONS

"Stabilet® From Hill–Rom®" Product Brochure, six pages, 1992.
"Stabilet CC™ From Hill–Rom®" Product Brochure, six pages, 1992.
"The Stabilet™ Freestanding Warmer and Clinical Bassinet From Hill–Rom®" Product Brochure, four pages, 1993.
"A Hill–Rom Solution, Stabilet 2000C, Stabilet CC, Stabilet Freestanding Infant Warmer Accessories" Product Brochure, eight pages, 1995.
"ISOLETTE® Infant Incubator . . . The Essence of Incubation", Air–Shields, Inc. Product Brochure, eight pages, 1996.

*Primary Examiner*—John P. Lacyk
*Attorney, Agent, or Firm*—Barnes & Thornburg

[57] ABSTRACT

A patient-support apparatus includes a base and a patient-support surface carried above the base. The patient-support apparatus further includes an indicator and a unit having at least one of a noise sensor and a light sensor which generates a sensor data signal. The patient-support apparatus further includes a control system coupled to the indicator and the at least one sensor. The control system is configured to process the sensor data signal and activate the indicator only when the sensor data signal exceeds a preset threshold level. The patient-support apparatus further includes a mechanism coupled to the control system to permit adjustment of the preset threshold level.

44 Claims, 6 Drawing Sheets

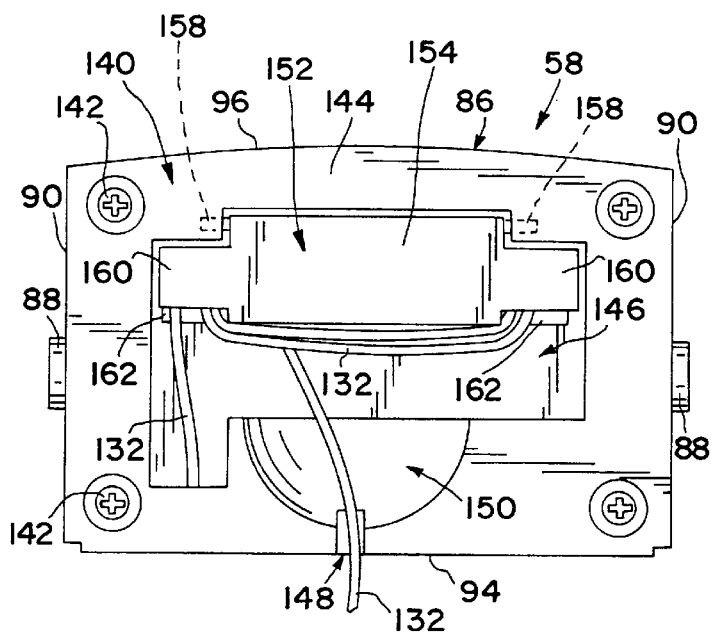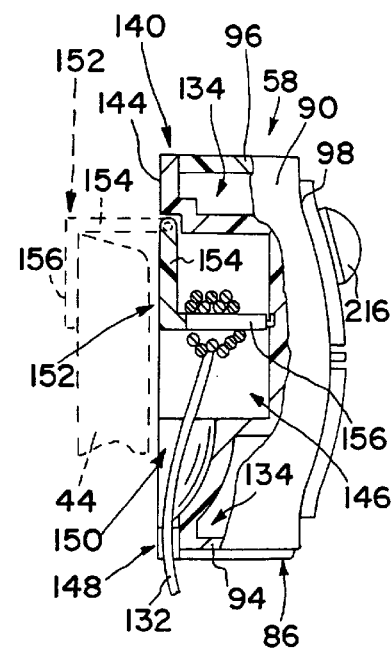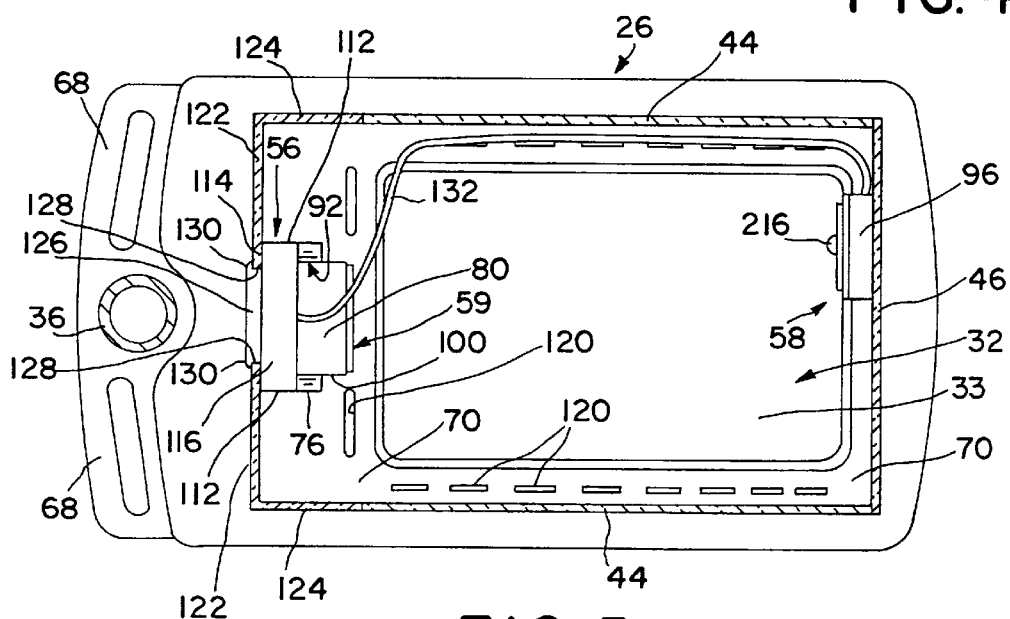
FIG. 3
FIG. 4
FIG. 5

NOISE AND LIGHT MONITOR APPARATUS

RELATED APPLICATIONS

This application is a continuation-in-part of application Ser. No. 08/533,371, filed Sep. 25, 1995, now U.S. Pat. No. 5,817,003, the specification of which is expressly incorporated herein by reference.

BACKGROUND AND SUMMARY OF THE INVENTION

The present invention relates to a patient-support apparatus, and particularly, to a thermal support apparatus of the type having an isolation chamber with a thermally controlled environment. More particularly, the present invention relates to a noise and light monitor apparatus for the thermal support apparatus.

Thermal support devices, such as infant warmers and incubators, having an isolation chamber and various systems that maintain and control a number of environmental parameters within the isolation chamber to facilitate the development of a premature infant are known. Infant thermal support devices conventionally include a patient-support surface for supporting the infant in the isolation chamber and some type of transparent enclosure arranged over the patient-support surface to enclose the isolation chamber. The enclosure typically includes movable panels, such as side panels with access ports and door panels that open to provide access to the patient in the isolation chamber through the access ports formed in the side panels.

Some infant warmers include either convective heaters or radiant heaters, or both, for warming the air in the isolation chamber. In addition, some infant warmers include a humidifier system for humidifying the air in the isolation chamber. Such infant warmers are typically provided with a control system that monitors the temperature and humidity of the air in the isolation. The control system adjusts the heaters and humidifier system so as to maintain desired temperature and humidity levels in the isolation chamber. Infant warmers having phototherapy apparatus that emit light within a specified frequency range to enhance the development of a premature infant are also known in the art.

It is known that exposing a premature infant to harsh external stimuli, such as high noise levels and high light levels, is not conducive to the development of the infant. Thus, it is desirable for noise and light levels to be maintained below certain threshold levels to prevent the developing infant from being disturbed. In addition, it has been found that coordinating the light levels to which the infant is exposed with the natural biological clock of the infant facilitates the development of the infant. What is needed is a patient-support apparatus having a noise and light monitor apparatus and some type of indicator that alerts a caregiver when noise or light levels exceed predetermined threshold levels so that the caregiver can take appropriate steps to reduce the noise or light levels to which the infant is exposed.

According to the present invention, a patient-support apparatus of the type having a base and a patient-support surface supported above the base is provided. The patient-support apparatus includes an indicator and a control system for processing sensor data and activating the indicator. The patient-support apparatus also includes a unit having at least one of a noise sensor and a light sensor. The control system provides an operative connection between the indicator and the at least one sensor. In addition, the at least one sensor provides sensor data to the control system.

In a preferred embodiment, the unit of the patient-support apparatus includes both a noise sensor and a light sensor and the control system provides an operative connection between the indicator and both the noise sensor and the light sensor. In addition, the control system is configured so that a caregiver can adjust the threshold noise and light levels within respective predetermined ranges. The indicator is activated when either the noise level or the light intensity level exceeds the respective selected threshold level. The indicator is preferably an alert light that flashes when activated by the control system. The alert light is mounted to a canopy that extends over the patient-support surface.

The patient-support apparatus of the present invention includes a base and a patient support carried above the base. The patient support includes a top surface and a tower extending upwardly from the top surface. The unit includes a box containing the noise and light sensors and the box is configured to mount to the tower of the platform tub. The control system includes an electric circuit that is housed in the patient support and a cable that couples the noise and light sensors to the electric circuit. The cable is sufficiently long to allow the unit to be placed at any position on the patient-support surface.

The unit also includes a cord wrap member coupled to the box for pivoting movement between a first position situated in a cord recess formed in the box and a second position situated outside the cord recess. When the cord is wrapped on the cord wrap member and the cord wrap member is in the first position, the box can be mounted to the tower. The cord wrap member is configured so that, when the cord wrap member is in the second position and the cord is unwrapped from the cord wrap member, the unit can be mounted to a side guard panel of the patient-support apparatus by hooking the cord wrap member over a top edge of the side guard panel.

Additional features and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 3 is a rear elevation view of the noise and light monitor unit of FIG. 2 showing the noise and light monitor unit including a box having a cord recess formed therein and a cord wrap member around which the cord wraps, the cord wrap member being in a first position situated inside the cord recess;

FIG. 4 is a side elevation view of the noise and light monitor unit of FIG. 3, with portions broken away, showing the cord wrap member being movable between the first position (in solid) and a second position (in phantom), the cord wrap member being configured to hook onto either of the side guard panels when in the second position;

FIG. 5 is a top plan view of the patient-support apparatus of FIG. 1, with portions broken away, showing the cord having sufficient length to allow the noise and light monitor unit to be mounted to the end guard panel at a foot end of the patient support;

DETAILED DESCRIPTION OF THE DRAWINGS

Figure 1:
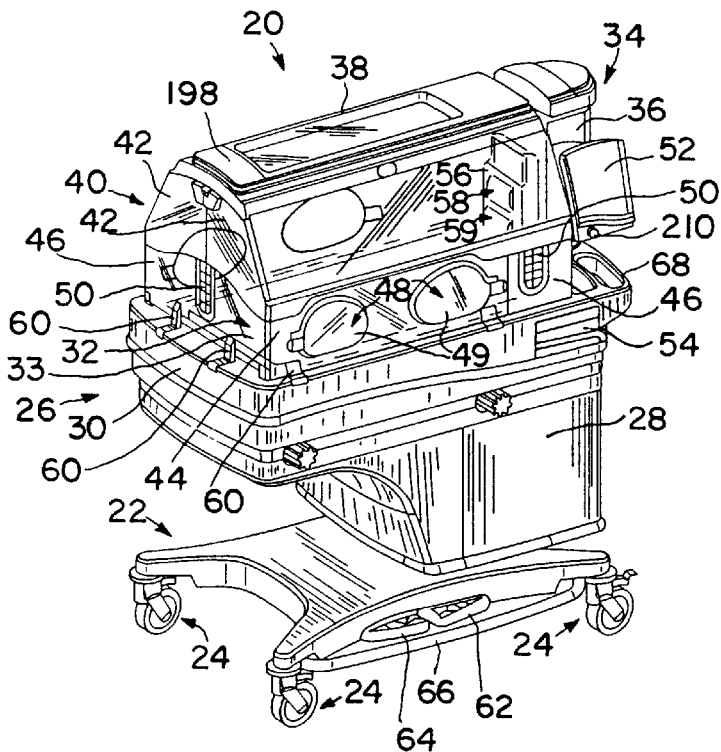
FIG. 1 is a perspective view of a patient-support apparatus according to the present invention showing a base, a patient support carried above the base, and an isolation chamber enclosed by an overlying canopy, a pair of transparent side guard panels, and a pair of transparent end guard panels.

A thermal support apparatus or patient-support apparatus 20, such as an infant warming device or incubator, includes a base 22, a plurality of castors 24 extending downwardly from base 22, and an infant supporting portion or patient support 26 supported above base 22 as shown in FIG. 1. Patient support 26 includes a pedestal 28 coupled to base 22 for vertical movement, a platform tub 30 supported by pedestal 28, and a mattress 32 supported on platform tub 30. Mattress 32 has an upwardly facing patient-support surface 33. Patient-support apparatus 20 also includes a canopy support arm 34 including a telescoping vertical arm 36 and a horizontal overhead arm 38. A canopy 40 is coupled to overhead arm 38 and is positioned to lie above platform tub 30. Canopy 40 includes a pair of canopy halves 42 coupled to overhead arm 38 for pivoting movement between a lowered position shown in FIG. 1 and a raised position (not shown).

A pair of transparent side guard panels 44 and a pair of transparent end guard panels 46 extend upwardly from platform tub 30 as shown in FIG. 1. Side guard panels 44 and end guard panels 46 cooperate with canopy halves 42 and overhead arm 38 to provide patient-support apparatus 20 with an isolation chamber. Side guard panels 44 are formed to include a pair of access ports that are normally closed by access door assemblies 48. Access door assemblies 48 include door panels 49 that can be opened to allow access to a patient, such as an infant, supported by thermal support apparatus 20 within the isolation chamber. Each end guard panel 46 is formed to include at least one U-shaped window and a pass-through grommet 50 is positioned to lie in each U-shaped window. Wires and tubes (not shown) can be routed into the isolation chamber through pass-through grommets 50.

Patient-support apparatus 20 includes a user interface panel 52 for monitoring various systems that control the temperature and humidity of the isolation chamber and for allowing caregivers to input various control parameters into memory of a control system of patient-support apparatus 20. Patient-support apparatus 20 also includes a humidifier module 54 that can be filled with water and inserted into a humidifier compartment of platform tub 30. Heated air is blown through humidifier module 54 and directed into the isolation chamber. A tower 56 is positioned to lie in the isolation chamber. Tower 56 supports various sensor modules or units, such as a noise and light monitor unit 58 and a patient environmental management (PEM) unit 59, and also provides a return-air path for the air being circulated through the isolation chamber.

Hinges 60 are provided so that side guard panels 44 and the end guard panel 46 at a foot end of patient support 26 can pivot downwardly away from canopy 40 to provide increased access to the infant supported by patient-support apparatus 20. Up and down buttons (not shown) can be pressed to extend and retract vertical arm 36 of canopy support arm 34, thereby raising and lowering, respectively, overhead arm 38 and canopy 40. Patient-support apparatus 20 includes an up pedal 62 that can be depressed to raise patient support 26 relative to base 22 and a down pedal 64 that can be depressed to lower patient support 26 relative to base 22. Patient-support apparatus 20 also includes a side bumper 66 that protects pedals 62, 64 and other components, such as base 22 and pedestal 28, from inadvertent impact. Platform tub 30 is formed to include a handle 68 on each side of canopy support arm 34. Handles 68 can be grasped by a caregiver to maneuver patient-support apparatus 20 during transport.

Other features of patient-support apparatus 20 are discussed in detail in co-pending applications Ser. No. 08/925,981 (attorney docket 7175-28091); Ser. No. 08/925,873 (attorney docket 7175-28750); Ser. No. 08/926,380 (attorney docket 7175-28751); and Ser. No. 08/926,383 (attorney docket 7175-28752), all of which are incorporated herein by reference.

Figure 2:
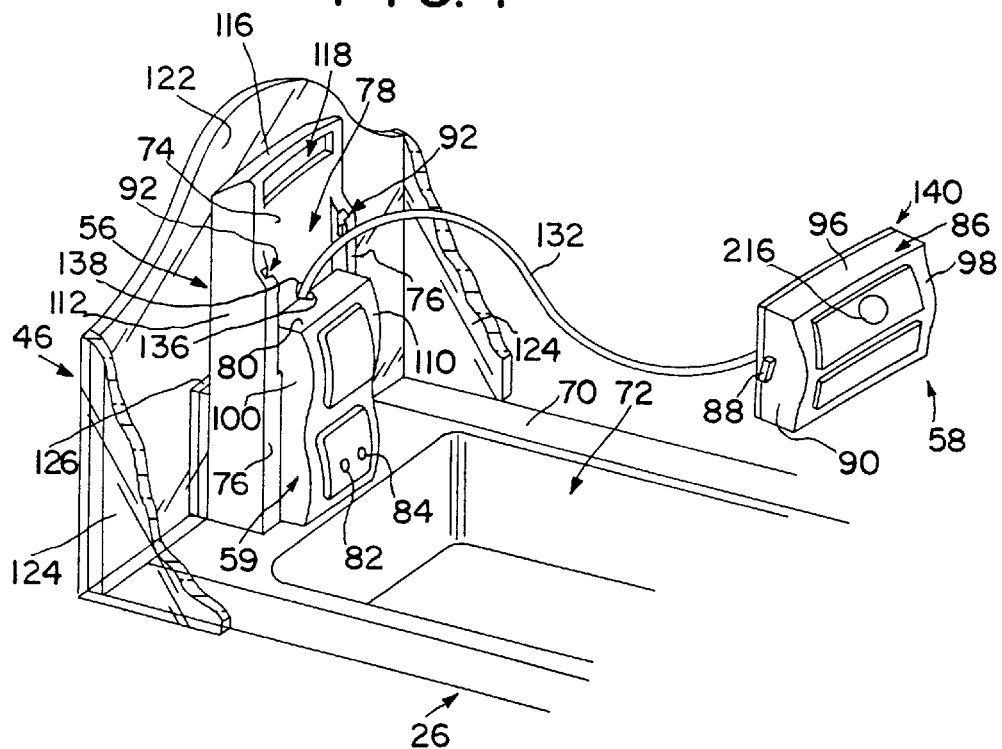
FIG. 2 is perspective view of the patient-support apparatus of FIG. 1, with portions broken away showing the patient support including an upper surface and a tower extending upwardly from the upper surface, one of the end guard panels having a transverse portion adjacent to the tower, a noise and light monitor unit spaced apart from the tower, and a cable extending between the tower and the noise and light monitor unit.

Patient-support apparatus 20 includes tower 56, noise and light monitor unit 58, and PEM unit 59 as previously described. Tower 56 extends upwardly from an upper surface 70 of patient support 26 adjacent to a mattress well 72 of platform tub 30 as shown in FIG. 2. Tower 56 includes a flat front wall 74 and a pair of vertical rails 76 appended to front wall 74. Rails 76 are transversely spaced apart to define a unit-receiving space 78 therebetween. PEM unit 59 is semi-permanently mounted to tower 56 so that a portion of PEM unit 59 is received in unit-receiving space 78 and a portion of PEM unit 59 is positioned to lie outside unit-receiving space 78.

PEM unit 59 has a bottom surface (not shown) abutting upper surface 70 of patient support 26 and an upwardly-facing top surface 80 as shown in FIG. 2. PEM unit 59 includes an interior compartment (not shown) in which PEM electronics are situated. PEM unit 59 includes a temperature probe connector port 84 to which one end of a temperature probe (not shown) connects to provide a patient-temperature reading through connector port 84 to the PEM electronics when another end of the temperature probe is attached to the patient. PEM unit 59 also includes a weigh scale connector port 82 to which a cord of a weigh scale (not shown) underlying mattress 32 is connected to provide a patient-weight reading through connector port 82 to the PEM electronics.

Noise and light monitor unit 58, hereinafter referred to as unit 58, includes a mouse or box 86 having a mounting lug 88 appended to each of a pair of side walls 90 thereof as shown in FIGS. 2 and 3. An upper end of each vertical rail 76 is formed to include a mounting notch 92 as shown in FIGS. 2 and 5. Unit 58 is selectively attachable to and detachable from tower 56. When unit 58 is attached to tower 56, a portion of unit 58 is received in unit-receiving space 78, a bottom wall 94 of box 86 rests upon upwardly-facing surface 80 of PEM unit 59, and lugs 88 are received in notches 92 to secure unit 58 to tower 56. Box 86 includes a top wall 96 and a front wall 98, each of which are positioned to lie outside unit-receiving space 78 when unit 58 is attached to tower 56.

PEM unit 59 includes a pair of transversely spaced-apart side walls 100 and a front wall 110 extending transversely between side walls 100 as shown in FIG. 2. When unit 58 is attached to tower 56 side walls 90 of box 76 are substantially coplanar with respective side walls 100 of PEM unit 59. In addition, front wall 110 of PEM unit 59 has a curved "double-lobed" contour and front wall 98 of unit 58 has a curved "single-lobed" contour that is substantially consistent with the curved "double-lobed" contour of front wall 110 of PEM unit 59. Thus, unit 58 nests within unit-receiving space 78 atop PEM unit 59 in an aesthetically pleasing manner when attached to tower 56.

Tower 56 provides a return-air path for the air being circulated through the isolation chamber as previously described. Tower 56 includes a pair of transversely spaced-apart side walls 112, each of which are integrally appended to front wall 74. Tower 56 also includes a back wall 114 appended to side walls 112 and an inclined top wall 116 integrally connecting walls 74, 112, 114 together. Walls 74, 112, 114, 116 are configured to provide tower 56 with an internal air passage and front wall 74 is formed to include a rectangular vent aperture 118 adjacent to top wall 116 as shown in FIG. 2. When unit 58 is attached to tower 56, top wall 96 of box 86 is positioned to lie beneath vent aperture 118 so that unit 58 does not obstruct vent aperture 118. An air circulation system of patient-support apparatus 20 includes a fan (not shown) in an internal compartment of platform tub 30. The fan operates to move air from the isolation chamber through vent aperture 118, into the internal air passage of tower 56, through channels (not shown) that surround mattress well 72, and then back into the isolation chamber through a plurality of air vent slots 120, shown in FIG. 5, formed in top surface 70 of patient support 26.

The end guard panel 46 at a head end of patient support 26 includes a large transverse panel 122 and a pair of small panels 124 that are appended to outer ends of panel 122 and that extend longitudinally from panel 122 toward the foot end of patient support 26 as shown in FIG. 2. Tower 56 includes a mounting plate 126 appended to back wall 114 as shown in FIGS. 2 and 5. Panel 122 is formed to include an edge 128, shown in FIG. 5, that defines a somewhat U-shaped mounting slot in panel 122. When mounting plate 126 of tower 56 is received in the mounting slot of panel 122, engagement of edge 128 of panel 122 with mounting plate 126, prevents transverse movement of panels 122, 124 relative to patient support 26. Mounting plate 126 is formed to include a pair of outwardly extending ribs 130 as shown in FIG. 5. Portions of panel 122 adjacent to edge 128 are trapped between ribs 130 and back wall of 114 of tower 56 so that longitudinal movement of panels 122, 124 relative to patient support 26 is prevented when mounting plate is received in the mounting slot of panel 122. Panels 122, 124 can be lifted upwardly relative to patient support 26 until mounting plate 126 is no longer received in the mounting slot of panel 122 and then panels 122, 124 can be separated away from patient support 26 and tower 56.

An electrical cord 132 connects unit 59 to PEM unit 59 as shown in FIGS. 2 and 5. Unit 58 includes noise and light monitor circuitry that is contained in an interior region 134, shown in FIG. 4, of box 86. Electrical cord 132 interconnects the PEM electronics that are housed in PEM unit 59 and the noise and light monitor circuitry that is housed in interior region 134 of box 86. Top wall 80 of PEM unit 59 is formed to include a notch 136 and front wall 74 of tower 56 is formed to include a notch 138 that is adjacent to notch 136 as shown in FIG. 2. A back wall (not shown) of PEM unit 59 abuts front wall 74 of tower 56 and electrical cord 132 is routed through notches 136, 138 and downwardly between PEM unit 59 and tower 56. Electrical cord 132 enters the interior compartment of PEM unit 59 though the back wall thereof. By routing electrical 132 in this manner, electrical cord 132 is prevented from inadvertently disconnecting from the PEM electronics.

Box 86 includes a back cover 140 coupled to walls 90, 92, 96, 98 by suitable fasteners, such as screws 142, which are arranged at the corners of back cover 140 as shown in FIG. 3. Back cover 140 includes a back surface 144 and a large cord recess 146 formed in the central region of back surface 144. In addition, back cover 140 includes a notch 148 formed in a perimetral potion of back surface 144 adjacent to bottom wall 92 and a transition recess 150 extending between notch 148 and cord recess 146 as shown in FIGS. 3 and 4. Back cover 140 seals against walls 90, 92, 96 to enclose interior region 134 of box 86.

Unit 58 includes a cord wrap member 152 having a first panel 154 and a second panel 156 appended to first panel 154 and extending therefrom in a perpendicular arrangement as shown in FIG. 4. Cord wrap member 152 is pivotably coupled to back cover 140 of box 86 by a pair of pivot posts 158 that are appended to first panel 154 as shown in FIG. 3. Cord wrap member 152 is pivotable between a stored position, shown in FIGS. 3 and 4, and a flipped-out position, shown in FIG. 4 (in phantom). When cord wrap member 152 is in the stored position, first panel 154 is flush with back surface 144 of back cover 140 and second panel 156 is positioned to lie inside recess 146. When cord wrap member 152 is in the flipped-out position, first panel 154 extends away from back cover 140 and second panel is positioned to lie outside recess 146.

First panel 154 includes a pair of oppositely extending tabs 160 and second panel 156 includes a pair of oppositely extending tabs 162 that are spaced apart from tabs 160 to define respective cord wrap spaces therebetween as shown in FIG. 3. When unit 58 is attached to tower 56, cord wrap member 152 is in the stored position having a majority of cord 132 wrapped around second panel 156 through the cord wrap spaces between tabs 160, 162. A portion of cord 132 is routed from cord recess 146 through transition recess 150, through notch 148, and into PEM unit 59 when unit 58 is mounted to tower 56. After cord 132 has been wrapped around second panel 156 of cord wrap member 152 as much as possible and before unit 58 is attached to tower 56, a small portion of cord 132 still extends from unit 58 to notches 136, 138. Transition recess 150 is spherically-shaped so that this small amount of cord 132 can move through notch 148 and into transition recess 150 during the final stages of attaching unit 58 to tower 56. When unit 58 is finally attached to tower 56, back surface 144 of back cover 140 abuts front wall 74 of tower 56 and a very small portion of cord 132 is received in notch 148.

When unit 58 is detached from tower 56, cord wrap member 152 is moved to the flipped-out position and cord 132 is unwrapped from second panel 156. Cord 132 is sufficiently long to allow unit 58 to be placed anywhere on patient-support surface 33 or the portion of upper surface 70 encompassed by side and end guard panels 44, 46. Cord wrap member 152 is configured to allow unit 58 to be hung along the top edge of either of side guard panels 44, as shown in FIG. 4 (in phantom), or along the top edge of either of end guard panels 46 as shown in FIG. 5. Cord wrap member 152 can be used to hang unit 58 on other structures (not shown) as well. Alternatively, after cord 132 is unwrapped from second panel 156, cord wrap member 152 can be returned to the stored position and unit 58 can be placed upon either mattress 32 or patient support 26 so that back surface 144 of back cover 140 abuts either surface 33 or surface 70, respectively.

Patient-support apparatus 20 includes PEM electronics situated in an internal compartment of PEM unit 59 and noise and light monitor circuitry situated in interior region 134 of box 86 as previously described. The PEM electronics and the noise and light monitor circuitry are each separate sub-portions of a large overall electrical system that is located throughout patient-support apparatus 20. A block diagram showing a portion 164 of the large overall electrical system of patient-support apparatus 20 that is associated with noise and light monitor unit 58, hereinafter referred to as circuit 164, is illustrated in FIG. 6.

Figure 6:
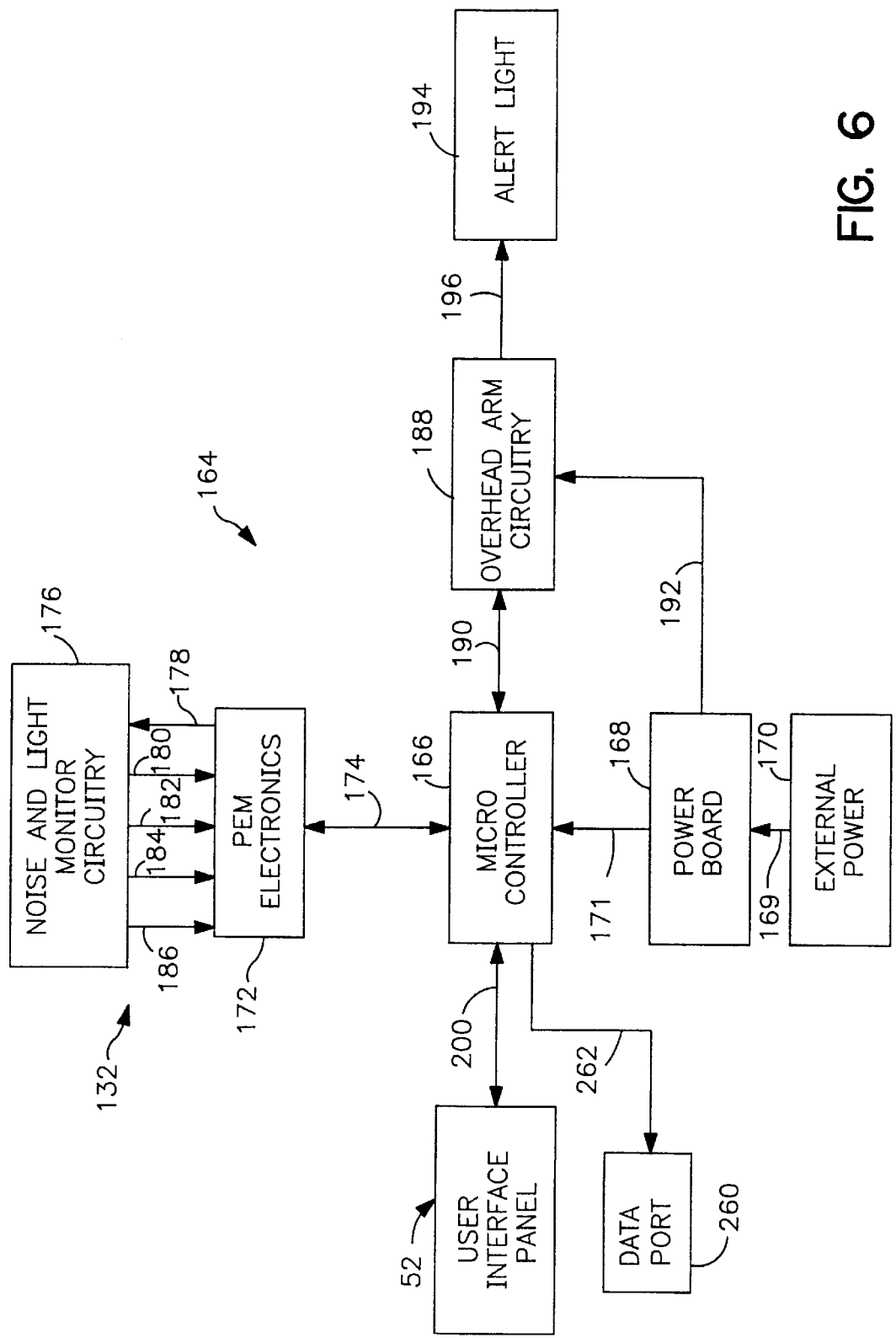
FIG. 6 is a block diagram of the portion of an electrical system of the patient-support apparatus of FIG. 1 associated with the noise and light monitor unit.

Circuit 164 includes a microcontroller 166 that receives power from a power board 168 as shown in FIG. 6. Microcontroller 166 is a microprocessor based controller having various input ports for receiving signals from other components of the overall electrical system and various output ports for sending signals to other components of the overall electrical system as is described in detail in application Ser. No. 08/533,371, filed Sep. 25, 1995, the specification of which is expressly incorporated herein by reference. Power board 168 receives power via a power line 169 from external power, indicated by block 170 of FIG. 6. External power 170 is standard 120 Volt AC power. Power board 168 includes conventional circuitry that converts the supplied external power into, for example, ±12 Volt DC and ±5 Volt DC power which is suitable for operating the various electrical circuit components contained in microcontroller 166 and contained elsewhere in the overall electrical system. Power board 168 supplies the converted power to microcontroller 166 via a power line 171.

Figure 7:
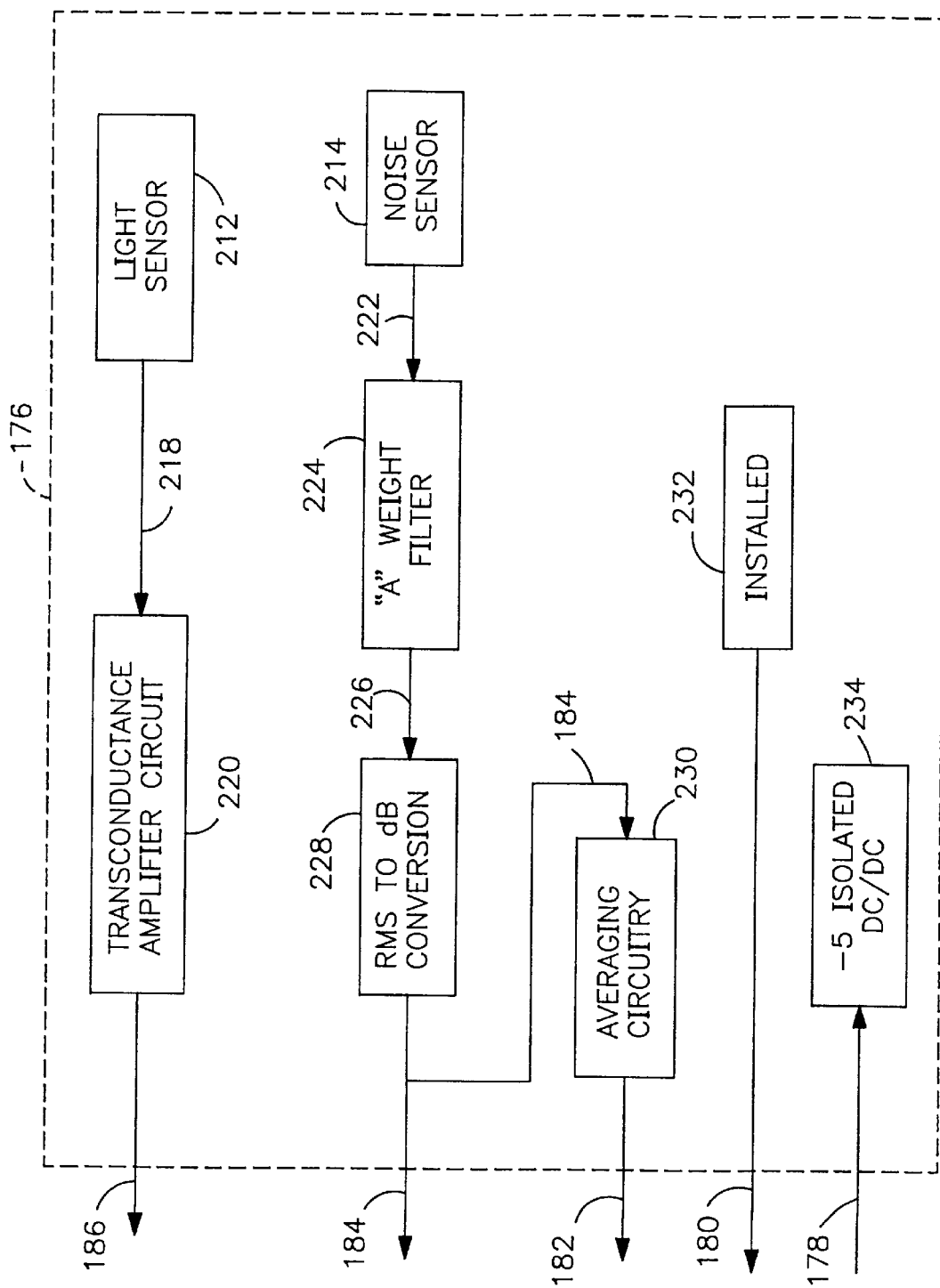
FIG. 7 is a block diagram of a sub-portion of the electrical system contained within the noise and light monitor unit.
Figure 8:
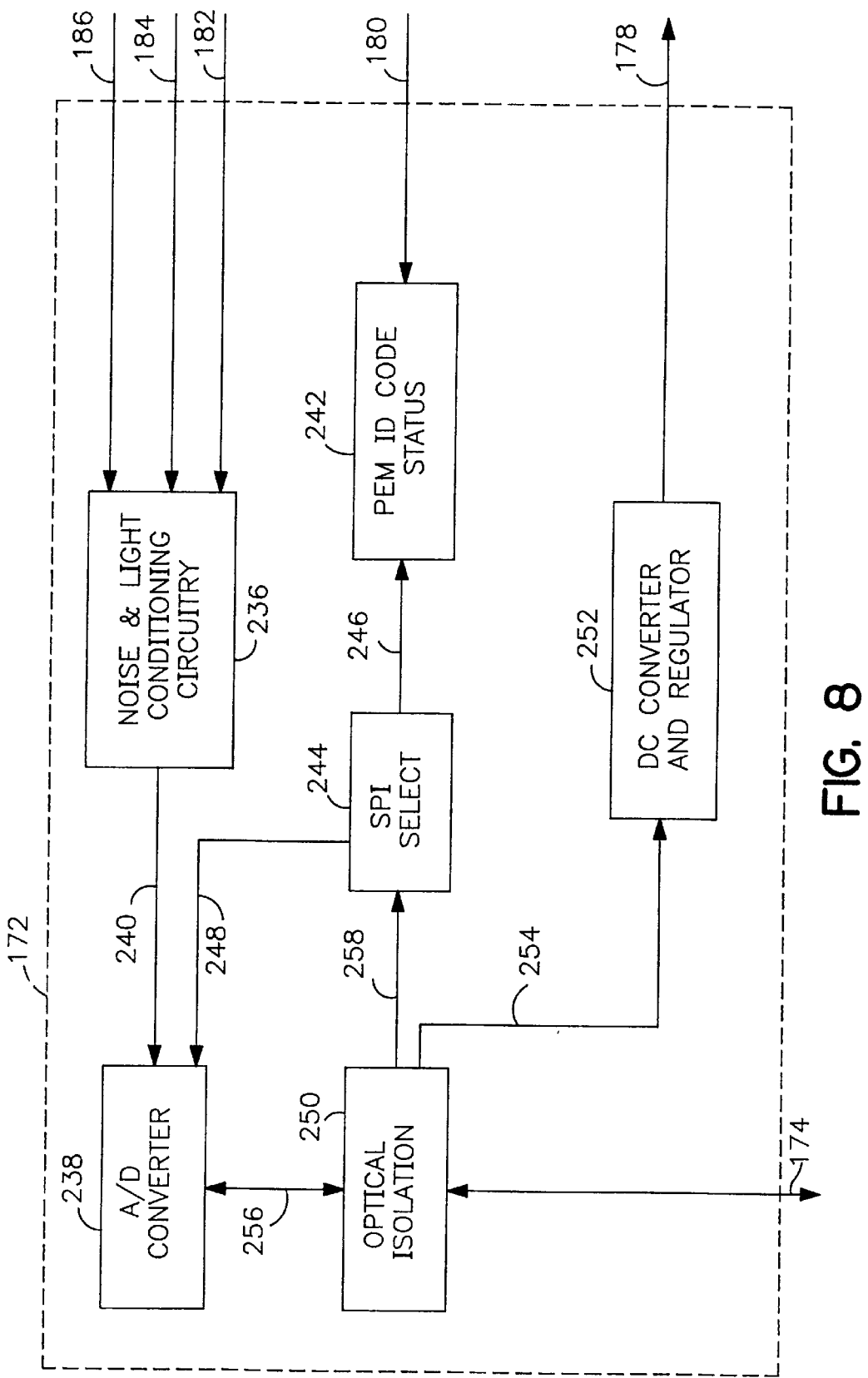
FIG. 8 is a block diagram of a sub-portion of the electrical system contained within a patient environmental management unit of the electrical system.

Microcontroller 166 is coupled to the PEM electronics, indicated by block 172 in FIGS. 6 and 8, by a combined power and data line 174. Control data and sensor data is transmitted between microcontroller 166 and PEM electronics 172 via line 174 and power for the PEM electronics 172 is supplied from microcontroller 166 to PEM electronics 172 via line 174 as well. The noise and light monitor circuitry, indicated by block 176 in FIGS. 6 and 7, is coupled to PEM electronics 172 by cord 132 as previously described. Cord 132 includes a power line 178 over which +5 Volt DC power is supplied to noise and light monitor circuitry 176. Cord 132 also includes wires over which an "installed" signal 180, an "average noise" signal 182, a "peak noise" signal 184, and a "light intensity" signal 186 are sent to PEM electronics 172 from noise and light monitor circuitry 176, hereinafter referred to as monitor circuitry 176.

Although monitor circuitry 176 is coupled to PEM electronics 172 by cord 132, other means for coupling monitor circuitry 176 to PEM electronics 172 or to any other portion of circuit 164 are possible. For example, in an alternative embodiment, unit 58 is a cordless unit having a transmitter that transmits data to a receiver on patient-support apparatus 20 in a conventional manner, such as by use of infrared signals, radio frequency signals, or ultrasonic signals. The receiver then couples to circuit 164 to provide signal inputs to circuit 164.

Overhead arm 38 includes a number of compartments (not shown) in which overhead arm circuitry, indicated by block 188 in FIG. 6, is situated. Microcontroller 166 is coupled to overhead arm circuitry 188 by a data line 190. Control data and feedback data is transmitted between microcontroller 166 and overhead arm circuitry 188 via line 190. In addition, power board 168 is coupled to overhead arm circuitry 188 by a power line 192. Overhead arm 38 also includes a compartment (not shown) in which an alert light, indicated by block 194 in FIG. 6, is situated. In a preferred embodiment, alert light 194 is a white light that is covered by a slightly opaque light cover 198, shown in FIG. 1. Alert light 194 is coupled to overhead arm circuitry 188 by an ON/OFF line 196.

User interface panel 52 is coupled to microcontroller 166 via a data line 200 as shown in FIG. 6. User interface panel 52 includes a keypad, an LED display screen, and an LCD display screen (all of which are not shown). User interface panel 52 also includes a rotatable knob 210 as shown in FIG. 1. Knob 210 is used to scroll through various menus that are displayed on the LCD display screen and buttons of the keypad are pressed to adjust various parameters that are stored in memory of microcontroller 166. Thus, user interface panel 52 permits a caregiver to input information into microcontroller 166 through data line 200. In addition, microcontroller 166 transmits data, such as temperature and humidity readings, to user interface panel 52 and the data is displayed to the caregiver on the LED screen of user interface panel 52.

One of the menu screens that can be selected by rotation of knob 210 allows the caregiver to input a noise threshold level and a light threshold level. In addition, the caregiver is permitted to select whether the noise threshold level is with respect to a peak noise level or an average noise level. In a preferred embodiment, the caregiver can select a light threshold level that is anywhere between about 20 ft. candles and about 250 ft. candles (about 200 lux and about 2700 lux) and the caregiver can select a noise threshold level that is anywhere between about 30 dBA and about 120 dBA. Circuit 164 operates so that, when either of the selected noise and light threshold levels is exceeded, alert light 194 is flashed to alert the caregiver of the situation. Thus, alert light 194 provides patient-support apparatus 20 with a noise and light indicator.

Monitor circuitry 176 includes a light sensor, indicated by block 212 in FIG. 7, and a noise sensor, indicated by block 214 in FIG. 7. In a preferred embodiment, light sensor 212 is a commercially available Centronic Model No. BPW-21P photodiode and noise sensor 214 is a commercially available Gentex Model No. 3072 microphone. Light sensor 212 is covered by a substantially transparent, protective dome 216 extending from front wall 98 of box 86 as shown in FIGS. 2, 4, and 5. In addition, front wall 98 of box 86 is formed to include a small aperture (not shown) through which sound waves travel to reach noise sensor 214.

Light sensor 212 produces an output signal 218, shown in FIG. 7, the magnitude of which is based upon the intensity of the light that passes through protective dome 216 and reaches light sensor 212. Monitor circuitry 176 includes a transconductance amplifier circuit, indicated by block 220 of FIG. 7. Output signal 218 is amplified by transconductance amplifier circuit 220 to produce light intensity signal 186 which is coupled to PEM electronics 172 as previously described.

Noise sensor 214 produces an output signal 222, shown in FIG. 7, the magnitude of which is based upon the sound pressure level of the sound waves that pass through the small aperture in front wall 98 of box 86 and reach noise sensor 214. Monitor circuitry 176 includes an "A" weight filter, indicated by block 224 of FIG. 7. Filter 224 is constructed to comply with ISO "A" weighting standards which relate to converting AC voltage signals to dBA signals and which are well known to those skilled in the art. Filter 224 converts output signal 222 into a filtered signal 226 which is coupled to an RMS-to-dB conversion circuit, indicated by block 228 of FIG. 7.

RMS-to-dB conversion circuit 228 converts filtered signal 226 into peak noise signal 184 which is, in turn, coupled to PEM electronics 172 as previously described. Peak noise signal 184 is also coupled to averaging circuitry, indicated by block 230 of FIG. 7. Averaging circuitry 230 converts peak noise signal 184 into average noise signal 182 which is, in turn, coupled to PEM electronics as also previously described. Monitor circuitry 176 further includes an installed connector port, indicated by block 232 of FIG. 7, and −5V isolated DC/DC circuitry, indicated by block 234 of FIG. 7. Installed connector port 232 is an active-low terminal that couples to ground to produce installed signal 180. DC/DC circuitry 234 routes power from power line 178 to various components of monitor circuitry 176 and also operates to "float" monitor circuitry 176 relative to true ground. Floating monitor circuitry 176 in this manner prevents the patient supported by patient-support apparatus 20 from receiving inadvertent electrical shocks from the electrical components of unit 58.

PEM electronics 172 includes noise and light conditioning circuitry, indicated by block 236 of FIG. 8. Signals 182, 184, 186 are coupled to conditioning circuitry 236 as are additional signals (not shown) from other types of patient environmental sensors, such as temperature and humidity sensors. Signals 182, 184, 186 are analog signals, each of which are modified by conditioning circuitry 236 to respective signals of appropriate dynamic range. PEM electronics 172 includes an A/D convertor, indicated by block 238 of FIG. 8. A/D convertor 238 receives the modified signals 182, 184, 186, as well as additional signals, via a data line 240 which, for the sake of simplicity, has been illustrated as a single line that carries all of the modified signals 182, 184, 186.

PEM electronics 172 includes a PEM ID code status circuit, indicated by block 242 of FIG. 8. Signal 180 from monitor circuitry 176 is coupled to code status circuit 242 along with other signals (not shown) from other components of the overall electrical circuit, such as a weigh scale and a baby temperature probe. PEM electronics 172 also includes a serial port interface (SPI) select circuit, indicated by block 244 of FIG. 8. SPI select circuit 244 provides a first selection signal 246 to code status circuit 242 and a second selection signal 248 to A/D converter 238. The first and second selection signals 246, 248 are controlled to coordinate the timing and sequence of the data that is ultimately transmitted to microcontroller 166 from PEM electronics 172 on power and data line 174.

PEM electronics 172 further includes an optical isolation circuit, indicated by block 250 of FIG. 8. Optical isolation circuit 250 is coupled to microcontroller 166 via power and data line 174. Optical isolation circuit 250 is also coupled to a DC converter and regulator, indicated by block 252 of FIG. 8, by a power line 254. Optical isolation circuit 250 routes power from power and data line 174 through power line 254 to DC converter and regulator 252 which then routes power to various components of PEM electronics 172. DC converter and regulator 252 also routes power to monitor circuit 176 on power line 178.

Optical isolation circuit 250 is coupled to A/D converter 238 via a sensor data line 256. In addition, optical isolation circuit 250 is coupled to SPI select circuit 244 via a coordination data line 258. Patient environment signals, such as those indicating the noise and light levels sensed by noise sensor 214 and light sensor 212, are transmitted from A/D converter 238 to optical isolation circuit 250 on sensor data line 256. Optical isolation circuit 250 then operates to forward the patient environment signals to microcontroller 166 on power and data line 174. Microcontroller 166 sends a coordination signal to optical isolation circuit 250 on line 174 and optical isolation circuit 250 operates to forward the coordination signal to SPI select circuit 244 on coordination data line 258. The coordination signal from microcontroller 166 indicates to PEM electronics 172 which patient environment signal to send back to microcontroller 166. The primary purpose of optical isolation circuit 250 is to "float" PEM electronics 176 relative to true ground. Floating PEM electronics in this manner prevents the patient supported by patient-support apparatus 20 from receiving inadvertent electrical shocks from the electrical components of PEM electronics 172.

Circuit 164 includes a data port, indicated by block 260 of FIG. 6, which is coupled to microcontroller 166 via a data line 262. Microcontroller 166 sends the patient environment signals received from PEM electronics 172 to data port 260. External data collection and display equipment (not shown) can be connected to circuit 164 at data port 260 and the patient environment signals can be recorded so that caregivers can study, for example, the time history of noise and light levels to which the patient is exposed.

Microcontroller 166 is coupled to overhead arm circuitry 188 by data line 190 and overhead arm circuitry 188 is coupled to alert light 194 by ON/OFF line 196 as previously described. When noise sensor 214, in cooperation with the associated components of monitor circuitry 176 and PEM electronics 172, indicates to microcontroller 166 that the measured peak or average noise level exceeds the selected noise threshold level, microcontroller 166 sends a signal to overhead arm circuitry 188 to flash alert light 194. In addition, when light sensor 212, in cooperation with the associated components of monitor circuitry 176 and PEM electronics 172, indicates to microcontroller 166 that the measured light level exceeds the selected light threshold level, microcontroller 166 sends a signal to overhead arm circuitry 188 to flash alert light 194.

Figure 9:
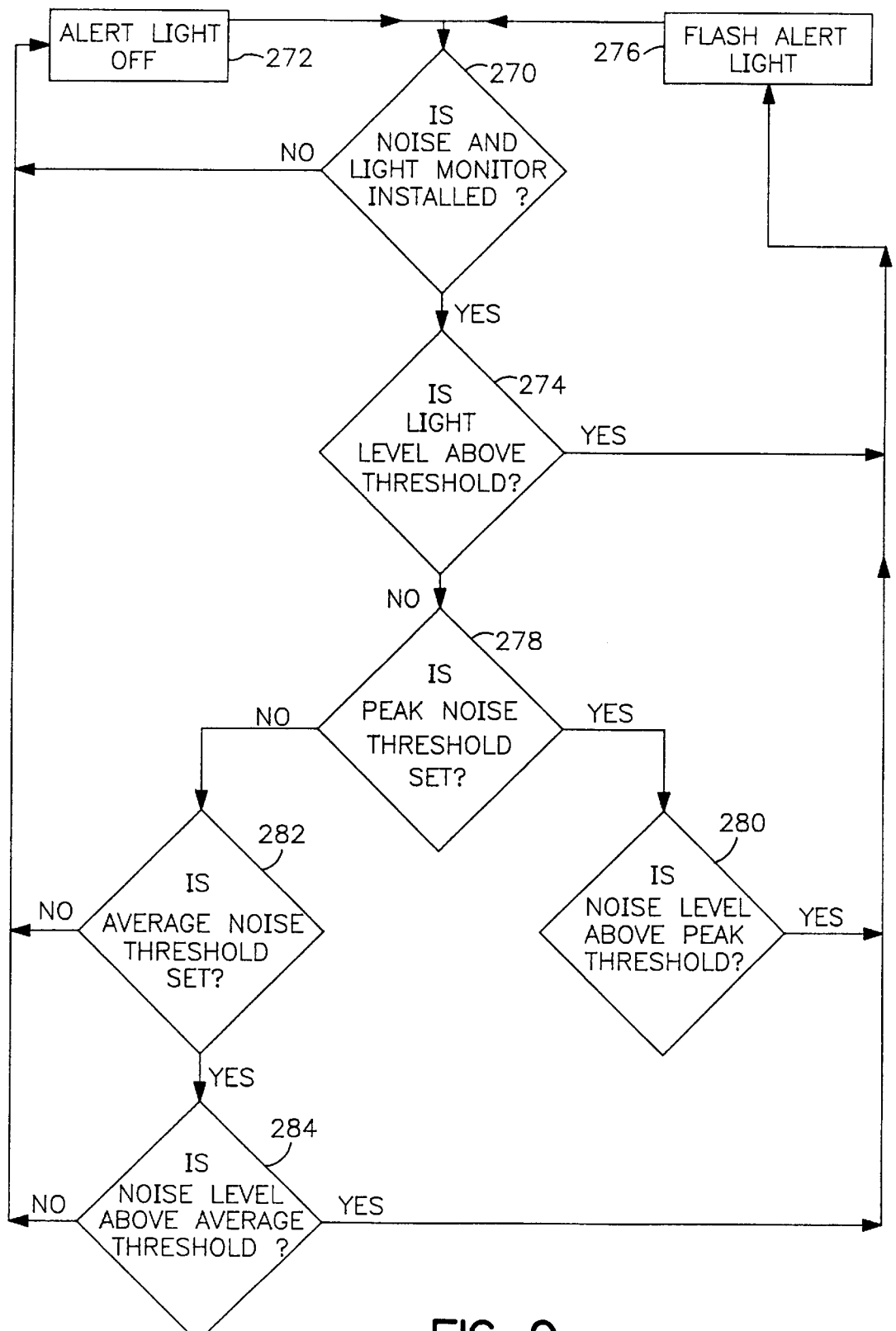
FIG. 9 is a flow chart illustrating the steps performed by the portion of the electrical system associated with the noise and light monitor unit.

FIG. 9 illustrates a flow chart of the steps performed by circuit 164 of patient-support apparatus 20 to determine whether to flash alert light 194. First, circuit 164 determines whether noise and light monitor unit 58 is installed, as indicated at block 270. If unit 58 is not installed, microcontroller 166 signals overhead arm circuitry 188 via line 190 and then, overhead arm circuitry 188 signals alert light 194 via line 196 to remain in an OFF condition, as indicated at block 272. If unit 58 is installed, circuit 164 determines at block 274 whether the light level sensed by sensor 212 is above the selected light threshold level. If the light level sensed by sensor 212 is above the selected light threshold level, microcontroller 166 signals overhead arm circuitry 188 via line 190 and then, overhead arm circuitry 188 signals alert light 194 via line 196 to alternately flash alert light 194 between ON and OFF conditions, as indicated at block 276.

If the light level is not above the selected light threshold level, circuit 164 determines at block 278 whether a caregiver has indicated that the peak noise level is the desired noise level to be monitored by circuit 164. If the peak noise level is the noise level to be monitored, circuit 164 determines at block 280 whether the noise level sensed by sensor 214 is above the selected peak noise threshold level. If the noise level sensed by sensor 214 is above the selected peak noise threshold level, microcontroller 166 signals overhead arm circuitry 188 via line 190 and then, overhead arm circuitry 188 signals alert light 194 via line 196 to alternately flash alert light 194 between ON and OFF conditions, as indicated at block 276. If the peak noise level sensed by sensor 214 is below the selected peak noise threshold level, microcontroller 166 signals overhead arm circuitry 188 via line 190 and then, overhead arm circuitry 188 signals alert light 194 via line 196 to remain in an OFF condition, as indicated at block 272.

If the peak noise level is not the noise level to be monitored, circuit 164 determines at block 282 whether a caregiver has indicated that the average noise level is the desired noise level to be monitored by circuit 164. If the average noise level is the noise level to be monitored, circuit 164 determines at block 284 whether the noise level sensed by sensor 214 is above the selected average noise threshold level. If the noise level sensed by sensor 214 is above the selected average noise threshold level, microcontroller 166 signals overhead arm circuitry 188 via line 190 and then, overhead arm circuitry 188 signals alert light 194 via line 196 to alternately flash alert light 194 between ON and OFF conditions, as indicated at block 276. If the average noise level sensed by sensor 214 is below the selected average noise threshold level, microcontroller 166 signals overhead arm circuitry 188 via line 190 and then, overhead arm circuitry 188 signals alert light 194 via line 196 to remain in an OFF condition, as indicated at block 272.

Although the invention has been described in detail with reference to a certain preferred embodiment, variations and modifications exist within the scope and spirit of the invention as described and as defined in the following claims.

We claim:

1. A patient-support apparatus comprising
   a base,
   a patient-support surface carried above the base,
   an indicator,
   a unit comprising at least one of a noise sensor and a light sensor which generates a sensor data signal,
   a control system coupled to the indicator and the at least one sensor, the control system being configured to process the sensor data signal and activate the indicator only when the sensor data signal exceeds a preset threshold level, and
   a mechanism coupled to the control system to permit adjustment of the preset threshold level.

2. The patient-support apparatus of claim 1, wherein the unit includes both a noise sensor and a light sensor and the control system provides an operative connection between the indicator and both the noise sensor and the light sensor.

3. The patient-support apparatus of claim 1, wherein the at least one sensor is a noise sensor for sensing a range of noise and the control system includes means for adjusting a threshold noise level above which the indicator is activated.

4. The patient-support apparatus of claim 3, wherein the range of noise sensed by the noise sensor is about 30 dBA to about 120 dBA.

5. The patient-support apparatus of claim 1, wherein the at least one sensor is a light sensor for sensing a range of light intensity, and the control system includes means for adjusting a threshold light intensity level at and above which the indicator is activated.

6. The patient-support apparatus of claim 5, wherein the range of light intensity sensed by the light sensor is about 20 ft. candles to about 250 ft. candles.

7. The patient-support apparatus of claim 1, wherein the indicator is a light that turns on when activated by the control system.

8. The patient-support apparatus of claim 7, wherein the light flashes when activated by the control system.

9. The patient-support apparatus of claim 8, wherein the light is a white light.

10. The patient-support apparatus of claim 7, wherein the light is a white light.

11. The patient-support apparatus of claim 7, further comprising an overhead structure supported above the patient-support surface and the light is mounted to the overhead structure.

12. The patient-support apparatus of claim 1, further comprising an overhead structure supported above the patient-support surface and the indicator is mounted to the overhead structure.

13. The patient-support apparatus of claim 1, further comprising a tower extending upwardly from the patient-support surface, the unit being configured to mount to the tower.

14. The patient-support apparatus of claim 13, wherein the control system includes a cable having a portion that extends from the unit to the tower.

15. The patient-support apparatus of claim 14, wherein the cable is sufficiently long to allow the unit to be placed at any position on the top surface of the patient support.

16. The patient-support apparatus of claim 14, wherein the unit includes a box for housing the at least one sensor and a cord wrap member coupled to the box for movement between a stored position received in a cord recess of the box and a flipped-out position outside the cord recess, and the cord is configured to wrap around the cord wrap member.

17. The patient-support apparatus of claim 13, wherein the unit includes a box having a pair of lugs, the tower is formed to include a pair of notches, and the lugs are received in the notches to mount the box to the tower.

18. The patient-support apparatus of claim 17, wherein the tower includes a pair of rails that are spaced apart to define a unit-receiving space therebetween, the notches are formed in the rails, and at least a portion of the box is received in the unit-receiving space when the unit is mounted to the tower.

19. The patient-support apparatus of claim 13, further comprising an air curtain generator for generating at least one air curtain above the patient support and the tower being formed to include a vent aperture through which at least a portion of the air curtain is drawn.

20. The patient-support apparatus of claim 19, wherein the unit includes a box for housing the at least one sensor and the box is mounted to the tower beneath the vent aperture.

21. The patient-support apparatus of claim 1, wherein the control system includes a receiver, the unit includes a transmitter coupled to the at least one sensor, and the transmitter transmits the sensor data signal to the receiver.

22. The patient-support apparatus of claim 1, wherein the mechanism is a user interface panel having a rotatable knob.

23. The patient-support apparatus of claim 3, wherein the noise level above which the indicator is activated corresponds to a peak noise level.

24. The patient-support apparatus of claim 3, wherein the noise level above which the indicator is activated corresponds to an average noise level.

25. The patient-support apparatus of claim 3, wherein the noise level above which the indicator is activated corresponds to a discomfort level that prevents a developing infant from being disturbed.

26. A patient-support apparatus comprising a base, a patient-support surface carried above the base for supporting a patient, a controller, an indicator coupled to the controller, a noise detector coupled to the controller, the controller being configured to provide an output signal to the indicator only upon detection by the noise detector of noise which exceeds a preset threshold level, and a mechanism coupled to the controller to permit adjustment of the preset threshold level.

27. The patient-support apparatus of claim 26, further comprising an electrical cord that couples the noise detector to the controller.

28. The patient-support apparatus of claim 26, wherein the controller includes a receiver, the noise detector includes a transmitter, and the transmitter transmits the output signal to the receiver.

29. The patient-support apparatus of claim 26, wherein the preset threshold level corresponds to a peak noise level.

30. The patient-support apparatus of claim 26, wherein the preset threshold level corresponds to an average noise level.

31. The patient-support apparatus of claim 26, wherein the preset threshold level corresponds to a discomfort level that prevents a developing infant from being disturbed.

32. The patient-support apparatus of claim 26, wherein the means for adjusting the preset threshold level is a user interface panel having a rotatable knob.

33. A patient-support apparatus comprising a base, a patient-support surface carried above the base for supporting a patient, a controller, an indicator coupled to the controller, a light detector coupled to the controller, the controller including a threshold device being configured to provide an output signal to the indicator only upon detection by the light detector of light which exceeds a preset threshold level, and a mechanism coupled to the controller to permit adjustment of the preset threshold level.

34. The patient-support apparatus of claim 33, further comprising an electrical cord that couples the light detector to the controller.

35. The patient-support apparatus of claim 33, wherein the controller includes a receiver, the light detector includes a transmitter, and the transmitter transmits the output signal to the receiver.

36. A patient-support apparatus comprising:

a base;

a patient support surface coupled to the base;

a tower extending upwardly adjacent the patient support surface, the tower being formed to include an accessory mounting portion;

an indicator;

a detector including at least one of a noise sensor and a light sensor, the detector being configured to generate an output signal, the detector being configured to be removably coupled to the mounting portion of the tower so that the detector is positionable in a first position coupled to the tower and a second position spaced apart from the tower; and a controller coupled to the indicator and the detector, the controller being configured to process the output signal and activate the indicator.

37. The apparatus of claim 36, further comprising a cable coupled between the detector and the controller, the cable having a portion that extends from the detector to the tower.

38. The patient-support apparatus of claim 37, wherein the cable is sufficiently long to allow the detector to be placed at any position on the patient support surface.

39. The apparatus of claim 37, wherein the detector includes a housing for the at least one sensor and a cord wrap member coupled to the housing for movement between a stored position received in a cord recess of the housing and a flipped-out position outside the cord recess, and the cable is configured to wrap around the cord wrap member.

40. The apparatus of claim 36, wherein the detector includes a housing having a pair of lugs, the tower is formed to include a pair of notches, and the lugs are received in the notches to mount the housing to the tower.

41. The apparatus of claim 40, wherein the tower includes a pair of rails that are spaced apart to define a receiving space therebetween, the notches are formed in the rails, and at least a portion of the housing is received in the receiving space when the detector is coupled to the tower.

42. The apparatus of claim 36, further comprising an air curtain generator configured to generate at least one air curtain above the patient support surface, and the tower is formed to include a vent aperture through which at least a portion of the air curtain is drawn.

43. The apparatus of claim 42, wherein the detector includes a housing for the at least one sensor, and the housing is mounted to the tower beneath the vent aperture.

44. The apparatus of claim 36, wherein the controller includes a receiver, the detector includes a transmitter coupled to the at least one sensor, and the transmitter transmits the output signal to the receiver.

* * * * *